United States Patent [19]

Holman et al.

[11] Patent Number: 5,224,939
[45] Date of Patent: Jul. 6, 1993

[54] SELF LOCKING GUIDE CATHETER

[75] Inventors: Thomas J. Holman, St. Louis Park; Henry J. Pepin, Loretto; William H. Penny, St. Anthony, all of Minn.

[73] Assignee: Scimed Life Systems, Inc., Maple Grove, Minn.

[21] Appl. No.: 888,748

[22] Filed: May 22, 1992

[51] Int. Cl.⁵ .............................................. A61M 25/00
[52] U.S. Cl. .................................................... 604/283
[58] Field of Search ................ 604/95, 165, 167, 241, 604/243, 256, 280–283; 128/657, 912; 285/81, 92

[56] References Cited

U.S. PATENT DOCUMENTS

| | | | |
|---|---|---|---|
| 4,191,185 | 3/1980 | Lemieux | 128/214.4 |
| 4,391,029 | 7/1983 | Czuba et al. | 29/450 |
| 4,547,194 | 10/1985 | Moorehead | 604/283 |
| 4,582,181 | 4/1986 | Samson | 128/348.1 |
| 4,785,858 | 11/1988 | Valentini et al. | 141/27 |
| 4,969,879 | 11/1990 | Lichte | 604/283 |
| 5,047,021 | 9/1991 | Utterberg | 604/283 |
| 5,053,015 | 10/1991 | Gross | 604/167 |
| 5,117,839 | 6/1992 | Dance | 604/165 |

FOREIGN PATENT DOCUMENTS 2650957  2/1991  France ................ 604/283

Primary Examiner—John D. Yasko
Assistant Examiner—Anthony Gutowski
Attorney, Agent, or Firm—Willian Brinks Olds Hofer Gilson & Lione

[57] ABSTRACT

A guide catheter in which the components of the hub include a ratchet mechanism that is operative to lock the hub components together and compress an integral flange of the catheter shaft therebetween to form a seal between the hub and catheter shaft without the use of bonding agents that will not become loosened accidently or inadvertently.

17 Claims, 1 Drawing Sheet

SELF LOCKING GUIDE CATHETER

BACKGROUND OF THE INVENTION

The present invention relates to catheters used in angioplasty.

In an angioplasty procedure, an accepted and well known medical practice, a catheter is placed into the vascular system of the patient, by first inserting a needle percutaneously into a blood vessel, and then inserting a guide wire through the needle lumen into the blood vessel. The guide wire is maneuvered and steered through the vascular system until its distal end extends past the area to be treated. The needle can then be removed leaving the guide wire in place. A guide catheter can then be threaded over the proximal end of the guide wire and advanced along it until its distal end approaches the area to be treated. A guide catheter includes an elongated tubular portion that is open at its distal end and has a hub at its proximal end. The hub can be gripped by the physician as an aid in maneuvering the guide catheter into its desired position. The lumen extending through the guide catheter has a diameter that is large enough to accommodate the balloon catheter in its un-inflated form. The connection between the elongated tubular portion and the hub of the guide catheter is subjected to considerable force as the catheter is twisted, pushed and pulled during the positioning procedure. Since the distal end is open, blood flows up the elongated tubular portion and could leak through the juncture if the seal is defective. Unnecessary blood loss by the patient can not, in the best interest of the patient as well as operating room personnel, be tolerated. Furthermore the physician must grip the guide catheter hub in the positioning procedure and if blood is leaking through this juncture it will be difficult for the physician to control the catheter. The blood that has entered the guide catheter is forced out its distal end when the guide catheter is removed, and it is thus important that the blood not become contaminated while in the guide catheter. If a bonding agent is used to seal the juncture between the elongated tubular portion and the hub it is possible that the bonding agent could make contact with the blood and contaminate it. Although the chance of contamination is low a reliable seal that does not use a bonding agent eliminates this possibility completely. In addition the proper application of a bonding agent is a difficult task in the assembly of guide catheters and when it is not properly applied or for some reason does not result in a complete bond the product will not pass inspection and the product must be scrapped.

After the guide catheter has been positioned the guide wire can be removed if desired or left in place. With the guide catheter in place the balloon catheter is threaded through the lumen of the guide catheter. It exits the distal end of the guide catheter at a point approaching the area to be treated. The uninflated balloon portion of the catheter is located within the artery such that it crosses the stenoses or reduced area. Pressurized inflation fluid is directed to the inflatable balloon through a lumen formed in the catheter to thus dilate the restricted area. The inflation fluid is generally a liquid and is applied at relatively high pressures. As the balloon is inflated it expands and forces open the stenoses or reduced area of the artery.

It is a primary objective of the present invention to provide a guide catheter that can be assembled without the use of bonding agents.

Another objective of the present invention is to provide a self locking guide catheter that locks the components of the hub together and to the elongated tubular portion such that they can not become loosened accidently or inadvertently.

Another objective of the present invention is to provide a guide catheter that has a conical surface in the gripping area to facilitate maneuvering of the catheter by the physician.

These and other objects and advantages of the present invention will no doubt become apparent to those skilled in the art after having read the following detailed description of the preferred embodiment which are contained in and illustrated by the various drawing figures.

SUMMARY OF THE INVENTION

To achieve these and other objectives, the present invention provides a new and unique catheter that includes a hub portion that can be assembled and secured to the elongated tubular portion without the use of bonding agents.

A preferred embodiment of the present invention includes a guide catheter having a hub that includes a luer segment portion and a central portion that seal the elongated tubular portion therebetween when they are connected.

An important advantage of the present invention is that the catheter can be assembled without the use of a bonding agent, is easier to assembly and a more reliable seal is accomplished. It is another advantage of the present invention that the catheter includes a conical surface in the gripping area.

These and other objects and advantages of the present invention will no doubt become apparent to those skilled in the art after having read the following detailed description of the preferred embodiment which are contained in and illustrated by the various drawing figures.

DETAILED DESCRIPTION OF THE PREFERRED EMBODIMENT

Figure 1:
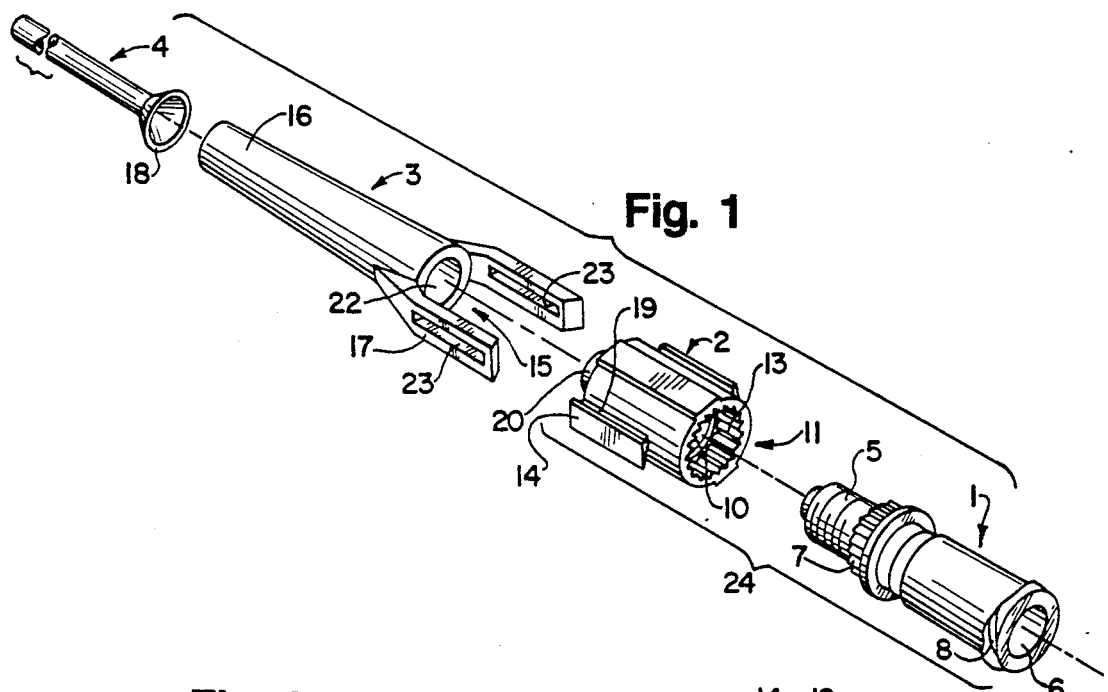
FIG. 1 is an exploded view of the self locking guide catheter.

FIG. 1 is an exploded view of the self locking guide catheter showing each component part isolated and aligned along the central axis of the guide catheter. It should be noted that, when assembling the component parts shown in this view, the guide catheter shaft 4 should first be inserted through the proximal end of the central segment 2 such that flared end 18 is located between concave frusta-conical surface 12 of central segment 2 and convex frusta-conical surface 9 of luer segment 1.

The luer segment 1 has a generally cylindrical shape and is molded as a single piece from rigid plastic material such as polycarbonate. A lumen 6 extends axially through the center of luer segment. The proximal end of lumen 6 includes a tapered section 29. An accessary such as a syringe can be connected to the proximal end of the guide catheter through a female luer lock that includes luer threads 8 and tapered section 29. The external screw threads 5 and external ratchet member 7 function to secure luer segment 1 to the central segment 2 and to the guide catheter shaft 4.

The central segment 2 which has a generally cylindrical shape is molded as a single piece from rigid plastic material such as polycarbonate. The central segment 2 has an internal port 11 extending centrally thereof. At the proximal end of internal port 11 there is an internal ratchet area 13 and distally of internal ratchet 13 is an area of internal screw threads 10. Distally of the internal screw threads 10 there is a concave frusta-conical surface 12 which is not seen in FIG. 1. A tubular extension 20 protrudes from the central distal end of central segment 2. A pair of longitudinally extending diametrically opposed members 14 having T-shaped cross sections protrude from the generally cylindrical shaped surface of the central segment 2. The diametrically opposed members 14 and the generally cylindrical surface of the central segment 2 form seats 19 over which the slotted ears 17 are received, as shall be discussed in greater detail.

When luer segment 1 has been connected to central segment 2 this subassembly is referred to as the control member 24. The luer segment 1 and central segment 2 function to secure the guide catheter shaft 4 to the control member 24. The securement of guide catheter shaft 4 to control member 24 is accomplished by locating the flared end 18 of guide catheter shaft 4 between the concave frusta-conical surface 12 of the central segment 2 and the convex frusta-conical surface 9 of the luer segment 1 with the distal end of guide catheter shaft 4 extending out the distal end of central segment 2. With the components so located luer segment 1 is threaded into central segment 2 through the engagement of external screw threads 5 with internal screw threads 10. This threaded engagement advances external ratchet member 7 toward internal ratchet area 13 and when this engagement is reached a ratchet effect occurs. The ratchet effect begins when the perpendicular distance between frusta-conical surfaces 9 and 12 is between two and ten times the wall thickness of the guide catheter shaft 4. The luer segment 1 can be advanced further toward central segment 2 to thus move convex frusta-conical surface 9 closer to concave frusta-conical surface 12 to thus tighten the seal on flared end 18, but once ratcheting starts luer segment 1 cannot be backed away from central segment 2. This is the self locking feature of this invention and has the advantage that once the seal between the guide catheter shaft 4 and the control member 24 has been made it cannot be lost as a result of vibrations or accidental unscrewing of one member relative to the other.

The strain relief/torquer 3 has the general shape of an externally tapered longitudinal member having a pair of rearwardly extending ears 17. The strain relief/torquer 3 is molded as a single piece from an elastomeric material such that it is relatively soft and elastic. The external conical surface 16 serves as a gripping area that the physician can grasp and roll through his or her finger and thumb to facilitate maneuvering of the guide catheter. The external conical surface 16 can be textured to further enhance maneuverability. The strain relief/torquer 3 has an internal port 15 that extends centrally through its entire length. At the proximal end of the internal port 15 there is formed an internal cylindrical surface portion 22 that is adapted to receive the tubular extension 20 of central segment 2. The rearwardly extending ears 17 have elongated slots 23 formed therein. The strain relief/torquer 3 also functions to relieve the strain that is placed on the guide catheter shaft 4 at the point where it exits the distal end of the central segment 2. A major longitudinal portion of the strain relief/torquer 3 closely surrounds the outer surface of the guide catheter shaft 4 and thus prevents the guide catheter shaft 4 from being kinked or bent sharply. The rearwardly extending ears 17 fit over the diametrically opposed members 14 of the central segment 2 into the seats 19. The thickness of rearwardly extending ears 17 is substantially equal to the upright portion of the T-shaped diametrically opposed members 14. The width of rearwardly extending ears 17 is greater than the width of the horizontal portion of the T-shaped diametrically opposed members 14. Since the rearwardly extending ears 17 are dimensioned such that they are wider than the width of the horizontal portions of the T-shaped diametrically opposed members 14 they function to pad the edges of the horizontal portions of the T-shaped members 14. Thus if the physician were to grasp the guide catheter in the area of the central segment 2 his or her fingers will encounter the soft elastomeric material of the ears 17 rather than the harder plastic material of the central segment 2.

Figure 2:
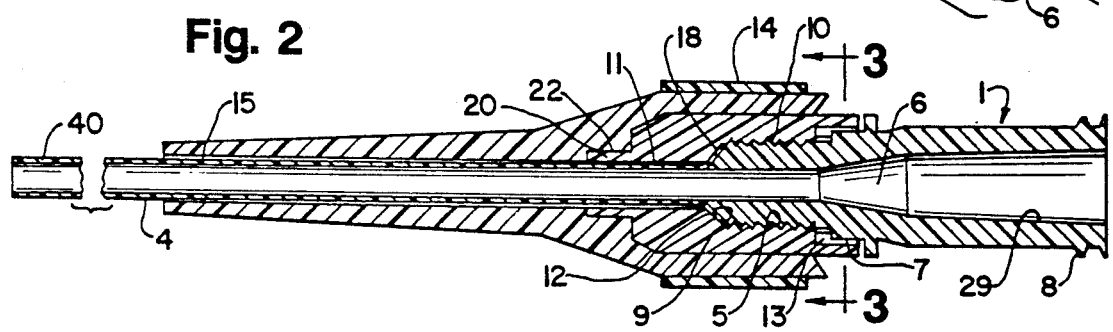
FIG. 2 is a cross sectional view of the assembled self locking guide catheter assembly in which some elements that cannot be seen in FIG. 1 are visible.

The guide catheter shaft 4 is made of a thermoplastic material and its proximal end is plastically deformed into a flared end by, for example placing the end over a heated mandrel. It is important that the flared end 18 be integral with the tubular portion of the guide catheter shaft 4 so that there can be no leakage at this intersection. As seen in FIG. 2 guide catheter shaft 4 is open at its distal end 40 and is of conventional design and functions in the conventional manner.

When the luer segment 1, central segment 2, strain relief/torquer 3 and guide catheter shaft 4 are assembled as described an assembly that will not leak has been accomplished, without the use of bonding agents. This assembly cannot vibrate loose or be accidentally or inadvertently loosened.

Referring now to FIG. 2, which is a cross sectional view of the assembled self locking guide catheter. It should be noted, that although FIG. 2 is a cross sectional view of the guide catheter, in the area of the diametrically opposed members 14 and pairs of ears 17 the cross section is offset slightly such that it passes though the longitudinally extending portions of the pairs of ears 17 rather than through the upright portion of the diametrically opposed members 14. The lumen 6 extends through the entire length of luer segment 1 however changes in diameter through its extent. The proximal end of the lumen 6 includes a tapered portion 29 which is intended to receive a male luer connector that is secured to the luer segment 1 by luer threads 8. There is illustrated a further conical reduction of the lumen 6 which reduces the diameter of lumen 6 to the inside diameter of the guide catheter shaft 4. The lumen 6, that begins in luer segment 1 continues through the remainder of the self locking guide catheter and is defined by the internal surface of guide catheter shaft 4. The convex frusta-conical surface 9 forms the distal end of 1.

The sealing relationship, previously discussed, between convex frusta-conical surface 9, flared end 18, and concave frusta-conical surface 12 can be best visualized in FIG. 2. For the purpose of clarity there is shown a gap between frusta-conical surface 9 and the surface of flared end 18 and between concave frusta-conical surface 12 and the surface of flared end 18. However it should be understood that when the guide catheter is assembled and in locked position, there are no gaps in these areas. In fact flared end 18 is compressed between convex frusta-conical surface 9 and concave frusta-conical surface 12 such that a seal is formed at this juncture that will withstand the high pressures that are encountered internally of the guide catheter. The luer segment 1 is connected to the central segment 2 by threading the external screw threads 5 of luer segment 1 into the internal screw threads 10 of central segment 2. This causes the external ratchet member 7 of luer segment 1 to approach the internal ratchet 13 of central segment 2. When external ratchet 7 engages internal ratchet 13 a ratcheting occurs between ratchet members 7 and 13 that will permit further movement of luer segment 1 into central segment 2 but will prevent the withdrawal of luer segment 1 from central segment 2. As is most clearly seen in FIG. 2, as convex frusta-conical surface 9 moves toward concave frusta-conical surface 12 the flared end 18 of guide catheter shaft 4 is sealed therebetween.

The internal port 15 of strain relief/torquer 3 has, at its proximal end, an internal cylindrical surface portion 22 that fits snugly over the tubular extension 20 of central segment 2 and the pairs of ears 17 are expanded to fit over the diametrically opposed members 14 and fit into the seats 19. As can be visualized in this view the connection between the pairs of ears 17 and the diametrically opposed members 14 function to hold the strain relief/torquer 3 in place on the central segment 2 and prevent axially movement therebetween. The functions of strain relief/torquer 3 relieving strain in the guide catheter shaft 4, can be best visualized with reference to FIG. 2. In the absence of relief/torquer 3 there would be a tendency for guide catheter shaft 4 to bend or kink at the point where it extends out of the distal end of the central segment 2. The strain relief/torquer 3 however surrounds the guide catheter shaft 4 in this area thus resisting bending and increasing the radius of curvature of bending that does occur thus making it difficult for the catheter shaft 4 to bend sharply or kink in this normally vulnerable area.

As can be seen in FIG. 2 the lumen 6 of luer segment 1 is continued through central segment 2 and strain relief/torquer 3 by the internal surface of guide catheter shaft 4 which passes through internal port 11 of central segment 2 and internal port 15 of strain relief/torquer 3.

Figure 3:
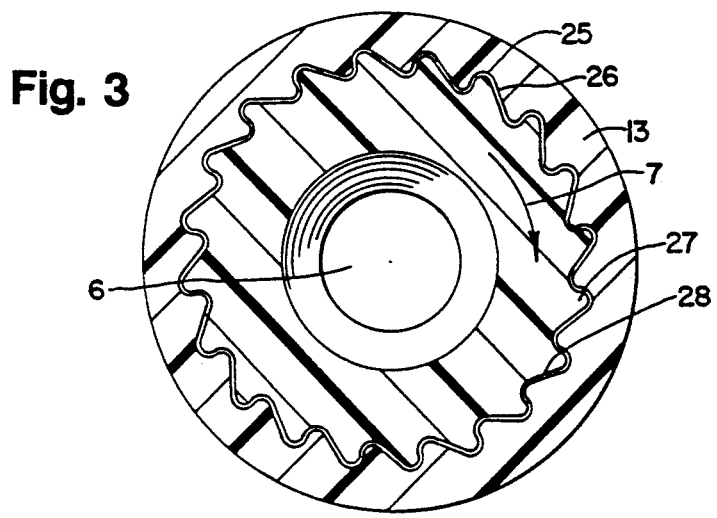
FIG. 3 is a cross sectional view taken along lines 3—3 of FIG. 2 and illustrates the ratchet mechanism of luer segment 1 and central segment 2.

FIG. 3 illustrates how the external ratchet 7 of luer segment 1 can be rotated in the clockwise direction relative to the internal ratchet 13 of central segment 2 but cannot be rotated in the opposite direction. As seen in FIG. 3 the internal ratchet 13 has a plurality of tooth shaped recessions 25 each including an inclined surface 26. The external ratchet 7 has a plurality of teeth 27 each including an inclined surface 28. The sleeve like portion of the central segment 2, that has the internal ratchet 13 formed on its internal surface, can flex sufficiently to allow inclined surfaces 28 of teeth 27 to slide up the inclined surfaces 26 of tooth shaped recessions 25 thereby flexing the sleeve like portion of central segment 2 outwardly sufficient for the teeth 27 to advance to the next tooth shaped recession 25. However if an attempt is made to rotate the external ratchet area member 7 in the counterclockwise direction the leading edges or points of teeth 27 will be urged into the bottom of tooth receiving shaped recessions 25 and rotation, in this direction, will be prevented.

Although the present invention has been described in terms of a specific embodiments, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A guide catheter device to be advanced through a patient's cardiovascular system toward a stenosis to be treated by angioplasty, comprising;

a luer segment, having a generally tubular shape and having a lumen extending axially therethrough, the distal end of said luer segment having a convex frusta-conical surface concentric to the lumen, external screw threads formed along the outer surface of said luer segment extending in the direction from the convex frusta-conical surface toward the proximal end of said luer segment, external ratchet members formed along the outer surface of said luer segment commencing beyond the proximal end of the external screw threads and extending toward the proximal end of said luer segment, a central segment, having a generally hollow tubular shape, the hollow of said central segment including a large diameter section commencing at the proximal end of the central segment and extending toward its distal end and a small diameter section commencing at the distal end of the central segment and extending toward its proximal end, said small diameter section being axially aligned with said lumen extending through the luer segment, a concave frusta-conical surface connecting the distal end of the large diameter section to the proximal end of the small diameter section, the concave frusta-conical surface being complementary to said convex frusta-conical surface, internal screw threads formed along the large diameter section commencing proximally to the concave frusta-conical surface and extending toward the proximal end of the central segment, said external and internal screw threads being dimensioned to mesh and causing the luer segment and central segment to telescope together, moving the concave and convex frusta-conical surfaces toward each other in response to relative rotation therebetween, an internal ratchet area formed along the large diameter section commencing proximally to the internal screw threads and extending toward the proximal end of the central segment, a guide catheter shaft having a lumen extending axially therethrough, said guide catheter shaft having a given wall thickness, the proximal end of said guide catheter shaft terminating in a frusta-conical flange having a shape complementary to said convex and concave frusta-conical surfaces, said flange portion being interposed between the convex and concave frusta-conical surfaces of the luer segment and central segment respectively, the external and internal ratchet areas being located relative to each other such that they advance toward each other as the luer segment and central segment telescope together and complete the engagement when the convex and concave frusta-conical surfaces are spaced from each other a distance equal to two to ten times the wall thickness of the guide catheter shaft, the external and internal ratchet areas being shaped such that relative rotation between the luer segment and central segment, in the direction causing the convex and concave frusta-conical surfaces to advance toward each other is permitted and rotation in the opposite direction is prevented.

2. The invention as set forth in claim 1, in which said luer segment has a luer segment fitting formed on its proximal end.

3. The invention as set forth in claim 1, in which said central segment includes a pair of diametrically opposed members extending outwardly therefrom and a tubular extension concentric with said small diameter section and extending axially from its distal end, said diametrically opposed members having T-shaped cross sections, said T-shaped cross sections including vertical upright portion connected at one end to the outer surface of said central segment and a horizontal cross portion at its other end, and a strain relief/torquer being formed of a material that is relatively soft and elastic, said strain relief/torquer including a hollow generally tubular shank portion, including a portion adapted to receive said tubular extension, and a portion adapted to closely receive and support said catheter guide shaft, said strain relief/torquer also including a pair of ears that protrude from the tubular shank portion in the proximal direction, the ears being wider than the horizontal cross portion of said diametrically opposed members, each ear having an elongated slot formed therein, said elongated slots being dimensioned to receive the vertical upright portion of said diametrically opposed members.

4. A catheter device to be advanced through a patient's cardiovascular system, comprising;

a luer segment, having a generally tubular shape and having a lumen extending axially therethrough, the distal end of said luer segment having a convex frusta-conical surface concentric to the lumen, external screw threads formed along the outer surface of said luer segment extending in the direction from the convex frusta-conical surface toward the proximal end of said luer segment, external ratchet members formed along the outer surface of said luer segment commencing beyond the proximal end of the external screw threads and extending toward the proximal end of said luer segment, a central segment, having a generally hollow tubular shape, the hollow of said central segment including a large diameter section commencing at the proximal end of the central segment and extending toward its distal end and a small diameter section commencing at the distal end of the central segment and extending toward its proximal end, a concave frusta-conical surface connecting the distal end of the large diameter section to the proximal end of the small diameter section, the concave frusta-conical surface being complementary to said convex frusta-conical surface, internal screw threads formed along the large diameter section commencing proximally to the concave frusta-conical surface and extending toward the proximal end of the central segment, said external and internal screw threads being dimensioned to mesh and causing the luer segment and central segment to telescope together, moving the concave and convex frusta-conical surfaces toward each other in response to relative rotation therebetween, an internal ratchet area formed along the large diameter section commencing proximally to the internal screw threads and extending toward the proximal end of the central segment, a catheter shaft having a lumen extending axially therethrough, said catheter shaft having a given wall thickness, the proximal end of said catheter shaft terminating in a flange portion, said flange portion being interposed between the convex and concave frusta-conical surfaces of the luer segment and central segment respectively, the external and internal ratchet areas being located relative to each other such that they advance toward each other as the luer segment and central segment telescope together and engage when the convex and concave frusta-conical surfaces are spaced from each other a distance equal to two to ten times the wall thickness of the catheter shaft, the external and internal ratchet areas being shaped such that relative rotation between the luer segment and central segment, in the direction causing the convex and concave frusta-conical surfaces to advance toward each other is permitted and rotation in the opposite direction is prevented.

5. The invention as set forth in claim 4, in which said luer segment has a luer fitting formed on its proximal end.

6. The invention as set forth in claim 4, in which said central segment includes a pair of diametrically opposed members extending outwardly therefrom and a tubular extension concentric with said small diameter section and extending axially from its distal end, said diametrically opposed members having T-shaped cross sections, said T-shaped cross sections including vertical upright portion connected at one end to the outer surface of said central segment and a horizontal cross portion at its other end, and a strain relief/torquer formed of a material that is relatively soft and elastic, said strain relief/torquer including a hollow generally tubular shank portion, including a portion adapted to receive said tubular extension, and a portion adapted to closely receive and support said catheter guide shaft, said strain relief/torquer also including a pair of ears that protrude from the tubular shank portion in the proximal direction, the ears being wider than the horizontal cross portion of said diametrically opposed members, each ear having an elongated slot formed therein, said elongated slots being dimensioned to receive the vertical upright portion of said diametrically opposed members.

7. A catheter device to be advanced through a patient's cardiovascular system, comprising;

a luer segment, having a generally tubular shape and having a lumen extending axially therethrough, the distal end of said luer segment having a convex frusta-conical surface concentric to the lumen, external screw threads formed along the outer surface of said luer segment extending in the direction from the convex frusta-conical surface toward the proximal end of said luer segment, a central segment, having a generally hollow tubular shape, the hollow of said central segment including a large diameter section commencing at the proximal end of the central segment and extending toward its distal end and a small diameter section commencing at the distal end of the central segment and extending toward its proximal end, a concave frusta-conical surface connecting the distal end of the large diameter section to the proximal end of the small diameter section, the concave frusta-conical surface being complementary to said convex frusta-conical surface, internal screw threads formed along the large diameter section commencing proximally to the concave frusta-conical surface and extending toward the proximal end of the central segment, said external and internal screw threads being dimensioned to mesh and causing the luer segment and central segment to telescope together, moving the concave and convex frusta-conical surfaces toward each other in response to relative rotation therebetween, said central segment includes a pair of diametrically opposed members extending outwardly therefrom and a tubular extension concentric with said small diameter section and extending axially from its distal end, said diametrically opposed members having T-shaped cross sections, said T-shaped cross sections including vertical upright portion connected at one end to the outer surface of said central segment and a horizontal cross portion at its other end, a catheter shaft having a lumen extending axially therethrough, the proximal end of said catheter shaft terminating in a flange portion, said flange portion being interposed between the convex and concave frusta-conical surfaces of the luer segment and central segment respectively, and a strain relief/torquer formed of a material that is relatively soft and elastic, said strain relief/torquer including a hollow generally tubular shank portion, including a portion adapted to receive said tubular extension, and a portion adapted to closely receive and support said catheter guide shaft, said strain relief/torquer also including a pair of ears that protrude from the tubular shank portion in the proximal direction, the ears being wider than the horizontal cross portion of said diametrically opposed members, each ear having an elongated slot formed therein, said elongated slots being dimensioned to receive the vertical upright portion of said diametrically opposed members.

8. The invention as set forth in claim 7, in which said luer segment has a luer fitting formed on its proximal end.

9. A catheter device to be advanced through a patient's cardiovascular system, comprising:

a control member, having a generally elongated shape and having a lumen extending axially therethrough, said lumen including a distal small diameter section connected to a proximal large diameter section by a concave frusta-conical surface, said control member including a pair of diametrically opposed members extending outwardly therefrom and a tubular extension concentric with said small diameter section and extending axially from its distal end, said diametrically opposed members having T-shaped cross sections, said T-shaped cross sections including vertical upright portion connected at one end to the outer surface of said control member and a horizontal cross portion at its other end, a catheter shaft having a lumen extending axially therethrough, the proximal end of said catheter shaft terminating in a flange portion, such that the proximal end of the catheter shaft can be placed in the control member with its flange portion in engagement with the concave frusta-conical surface of the control member, a strain relief/torquer formed of a material that is relatively soft and elastic, said strain relief/torque including a hollow generally tubular shank portion, including a portion adapted to receive said tubular extension, and a portion adapted to closely receive and support said catheter shaft, said strain relief/torquer also including a pair of ears that protrude from the tubular shank portion in the proximal direction, the ears being wider than the horizontal cross portion of said diametrically opposed members, each ear having an elongated slot formed therein, said elongated slots being dimensioned to receive the vertical upright portion of said diametrically opposed members.

10. The invention as set forth in claim 9, in which said control member has luer lock threads formed on its proximal ends.

11. A catheter device to be advanced through a patient's vascular system toward an area to be treated, comprising:

a luer segment, having a generally tubular shape and having a lumen extending axially therethrough, the distal end of said luer segment having a convex frusta-conical surface concentric to the lumen, external ratchet members formed along the outer surface of said luer segment, a central segment, having a generally hollow tubular shape, the hollow of said central segment including a large diameter section commencing at the proximal end of the central segment and extending toward its distal end and a small diameter section commencing at the distal end of the central segment and extending toward its proximal end, said small diameter section being axially aligned with said lumen extending through the luer segment, a concave frusta-conical surface connecting the distal end of the large diameter section to the proximal end of the small diameter section, the concave frusta-conical surface being complementary to said convex frusta-conical surface, an internal ratchet area formed along the large diameter section, a catheter shaft having a lumen extending axially therethrough, said catheter shaft having a given wall thickness, the proximal end of said guide catheter shaft terminating in a frusta-conical flange having a shape complementary to said convex and concave frusta-conical surfaces, said flange portion being interposed between the convex and concave frusta-conical surfaces of the luer segment and central segment respectively, said luer and central segments having cooperating gripping areas that facilitates closing the gap between the frusta-conical surfaces as the luer segment and central segment telescope together to secure the flange of the guide catheter shaft therebetween, the external and internal ratchet areas being located relative to each other such that they advance toward each other as the luer segment and central segment telescope together and complete the engagement when the convex and concave frusta-conical surfaces are spaced from each other a distance equal to two to ten times the wall thickness of the catheter shaft.

12. The invention as set forth in claim 11, in which there are external screw threads formed along the outer surface of said luer segment extending in the direction from the convex frusta-conical surface toward the proximal end of said luer segment, and internal screw threads, formed along the large diameter section of said central segment, commencing proximally to the concave frusta-conical surface and extending toward the proximal end of the central segment, said external and internal screw threads being dimensioned to mesh and causing the luer segment and central segment to telescope together, moving the concave and convex frusta-conical surfaces toward each other in response to relative rotation therebetween.

13. The invention as set forth in claim 11, in which said luer segment has a luer segment fitting formed on its proximal end.

14. The invention as set forth in claim 12, in which said luer segment has a luer segment fitting formed on its proximal end.

15. The invention as set forth in claim 11, in which said central segment includes a pair of diametrically opposed members extending outwardly therefrom and a tubular extension concentric with said small diameter section and extending axially from its distal end, said diametrically opposed members having T-shaped cross sections, said T-shaped cross sections including vertical upright portion connected at one end to the outer surface of said central segment and a horizontal cross portion at its other end, and a strain relief/torquer being formed of a material that is relatively soft and elastic,
   said strain relief/torquer including a hollow generally tubular shank portion, including a portion adapted to receive said tubular extension, and a portion adapted to closely receive and support said catheter guide shaft,
   said strain relief/torquer also including a pair of ears that protrude from the tubular shank portion in the proximal direction, the ears being wider than the horizontal cross portion of said diametrically opposed members, each ear having an elongated slot formed therein, said elongated slots being dimensioned to receive the vertical upright portion of said diametrically opposed members.

16. The invention as set forth in claim 12, in which said central segment includes a pair of diametrically opposed members extending outwardly therefrom and a tubular extension concentric with said small diameter section and extending axially from its distal end, said diametrically opposed members having T-shaped cross sections, said T-shaped cross sections including vertical upright portion connected at one end to the outer surface of said central segment and a horizontal cross portion at its other end, and a strain relief/torquer being formed of a material that is relatively soft and elastic,
   said strain relief/torquer including a hollow generally tubular shank portion, including a portion adapted to receive said tubular extension, and a portion adapted to closely receive and support said catheter guide shaft,
   said strain relief/torquer also including a pair of ears that protrude from the tubular shank portion in the proximal direction, the ears being wider than the horizontal cross portion of said diametrically opposed members, each ear having an elongated slot formed therein, said elongated slots being dimensioned to receive the vertical upright portion of said diametrically opposed members.

17. The invention as set forth in claim 13, in which said central segment includes a pair of diametrically opposed members extending outwardly therefrom and a tubular extension concentric with said small diameter section and extending axially from its distal end, said diametrically opposed members having T-shaped cross sections, said T-shaped cross sections including vertical upright portion connected at one end to the outer surface of said central segment and a horizontal cross portion at its other end, and a strain relief/torquer being formed of a material that is relatively soft and elastic,
   said strain relief/torquer including a hollow generally tubular shank portion, including a portion adapted to receive said tubular extension, and a portion adapted to closely receive and support said catheter guide shaft,
   said strain relief/torquer also including a pair of ears that protrude from the tubular shank portion in the proximal direction, the ears being wider than the horizontal cross portion of said diametrically opposed members, each ear having an elongated slot formed therein, said elongated slots being dimensioned to receive the vertical upright portion of said diametrically opposed members.

* * * * *